United States Patent [19]
Look et al.

[11] Patent Number: 5,512,999
[45] Date of Patent: Apr. 30, 1996

[54] METHOD FOR NONDESTRUCTIVE MEASUREMENT OF DISLOCATION DENSITY IN GAAS

[75] Inventors: David C. Look, Dayton; Millard G. Mier, Yellow Springs; John R. Sizelove, Dayton; Dennis C. Walters, Fairborn, all of Ohio

[73] Assignee: The United States of America as represented by the Secretary of the Air Force, Washington, D.C.

[21] Appl. No.: 399,246

[22] Filed: Mar. 6, 1995

[51] Int. Cl.[6] ............................. G01N 21/88; G01N 21/35
[52] U.S. Cl. ............................. 356/30; 356/432; 250/341.4
[58] Field of Search ............................. 356/30, 31, 432; 250/341.4

[56] References Cited

U.S. PATENT DOCUMENTS

| 5,008,542 | 4/1991 | Look et al. | 250/341 |
| 5,077,475 | 12/1991 | Moriya et al. | 356/30 |

OTHER PUBLICATIONS

M. G. Mier, D. C. Look, J. R. Sizelove, D. C. Walters and D. L. Beasley, Infrared Transmission Topography: Application to Nondestructive Measurement of Dislocation Density and Carrier Concentration in Silicon–Doped Gallium Arsenide Wafers, 1995, pp. 1–5.

D. C. Look, D. C. Walters, M. G. Mier and J. R. Sizelove, Nondestructive Mapping of Carrier Concentration and Dislocation Density in N+–Type GaAs, Appl. Phys. Lett. 65 (17), 24 Oct. 1994, Amer. Instit. of Physics, pp. 2188–2190.

Primary Examiner—Richard A. Rosenberger
Attorney, Agent, or Firm—Thomas L. Kundert

[57] ABSTRACT

A method for nondestructively measuring dislocation density in a GaAs wafer is disclosed in which an unetched GaAs wafer is tested for fractional transmission (T) of light at a plurality of points over its surface. A light beam from a suitable source such as a tungsten-halogen lamp is passed through a monochromator and focused by a lens on the wafer. The fractional transmission (T) of light through the wafer is detected and the absorption coefficient ($\alpha$) is calculated at each of the points from the detected values of the fractional transmission. Regions of dislocation density in the wafer are determined nondestructively from the absorption data by dividing the values of $\alpha$ into equal segments bounded by the minimum and the maximum calculated values. A histogram is plotted of the number of values of $\alpha$ in each segment versus the value of $\alpha$ at the midpoint of the segment. A reference $\alpha$ point is selected from the histogram coinciding with the point approximately at which the first minimum value of $\alpha$ occurs following the first maximum value of $\alpha$. A map of the coordinate positions of all the values of $\alpha$ that are less than or equal to the reference $\alpha$ has been found to correspond substantially identically to the regions of dislocation density in the wafer as confirmed later by measurements on an etched wafer. The regions of dislocation density become readily discernible and are in marked contrast to the undislocated regions when the $\alpha$ is calculated from the fractional transmission at a wavelength ($\lambda$) of 0.90±0.03 μm.

3 Claims, 6 Drawing Sheets

5,512,999

METHOD FOR NONDESTRUCTIVE MEASUREMENT OF DISLOCATION DENSITY IN GAAS

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention relates to GaAs wafers and particularly to a method for realizing nondestructive, whole-wafer dislocation maps of a polished conducting GaAs wafer.

2. Description of the Prior Art

Bulk n+ GaAs:Si wafers are used to fabricate a variety of devices such as lasers and solar cells. Up to this time, very little attention has been given to GaAs: Si whole-wafer materials characterization, in contrast to the case of semi-insulating (SI) GaAs, where a variety of whole-wafer characterization techniques have been developed. For the SI case, two of the important whole-wafer parameters are EL2 and dislocation (or etch pit) density.

Transmission maps have proved to be very useful in delineating variations of EL2 concentration, dislocation density, and stress in semi-insulating (SI) GaAs wafers. It has been possible in some cases to correlate transmission maps of material properties with maps of device properties from the same or an adjacent wafer. While the EL2 and stress measurements are nondestructive, the dislocation density measurements require a KOH etch to form etch pits at the surface. In contrast to the EL2 centers, which reduce the transmission by absorption, the etch pits reduce the transmission by scattering, however, both effects are easily quantifiable.

U.S. Pat. No. 5,008,542 discloses a method and system for measuring whole-wafer etch pit or dislocation density (pD) in which an etched GaAs wafer is tested for fractional transmission at a plurality of points over its surface. The fractional transmission (T) of light through the wafer is detected at a plurality of points, digitized and fed to a computer for storage. Two or more of the transmission values are selected for calibration and are compared with manually counted etch pit densities at the same locations on the wafer. From this calibration, together with an estimate of the average etch pit size (area), the values for fractional transmission in all regions of the wafer are converted directly to etch pit density.

A long sought goal in the semiconductor industry has been a convenient technique for nondestructive evaluation of dislocation density. However, none of the usual optical techniques have proved to be useful for this purpose so far. For n+ GaAs wafers used in the fabrication of lasers, solar cells, and other devices, it seems that very little whole-wafer characterization has been carried out. In n+ GaAs, EL2 is very small and not important, but the dislocations are even more important than in SI GaAs because they can lead to dark-line defects and other nonradiative recombination centers which are deleterious to lasers.

SUMMARY OF THE INVENTION

An object of the invention is to provide a method for nondestructively measuring whole-wafer dislocation density in GaAs.

It is another object of the invention to provide an automated, digitized method for realizing nondestructively, whole-wafer maps of a polished conducting GaAs wafer.

According to the invention, an unetched GaAs wafer is tested for fractional transmission (T) of light at a plurality of points over its surface. A light beam from a suitable source such as a tungsten-halogen lamp is passed through a monochromator and focused by a lens on the wafer. The fractional transmission (T) of light through the wafer is detected and the absorption coefficient ($\alpha$) is calculated at each of the points from the detected values of the fractional transmission. Regions of dislocation density in the wafer are determined nondestructively from the absorption data by dividing the values of $\alpha$ into equal segments bounded by the minimum and the maximum calculated values. A histogram is plotted of the number of values of $\alpha$ in each segment versus the value of $\alpha$ at the midpoint of the segment. A reference $\alpha$ point is selected from the histogram coinciding with the point approximately at which the first minimum value of $\alpha$ occurs following the first maximum value of $\alpha$. The reference $\alpha$ point typically separates two bell-shaped distributions in the histogram. A map of the coordinate positions of all the values of $\alpha$ that are less than or equal to the reference $\alpha$ has been found to correspond substantially identically to the regions of dislocation density in the wafer as confirmed later by measurements on an etched wafer. The regions of dislocation density become readily discernible and are in marked contrast to the undislocated regions when the values of $\alpha$ are calculated from the fractional transmission at a wavelength ($\lambda$) of 0.90±0.03 µm.

Other features and advantages of the invention will be apparent from the following description, drawings and claims, which show and describe an embodiment of the invention.

DETAILED DESCRIPTION

Figure 1:
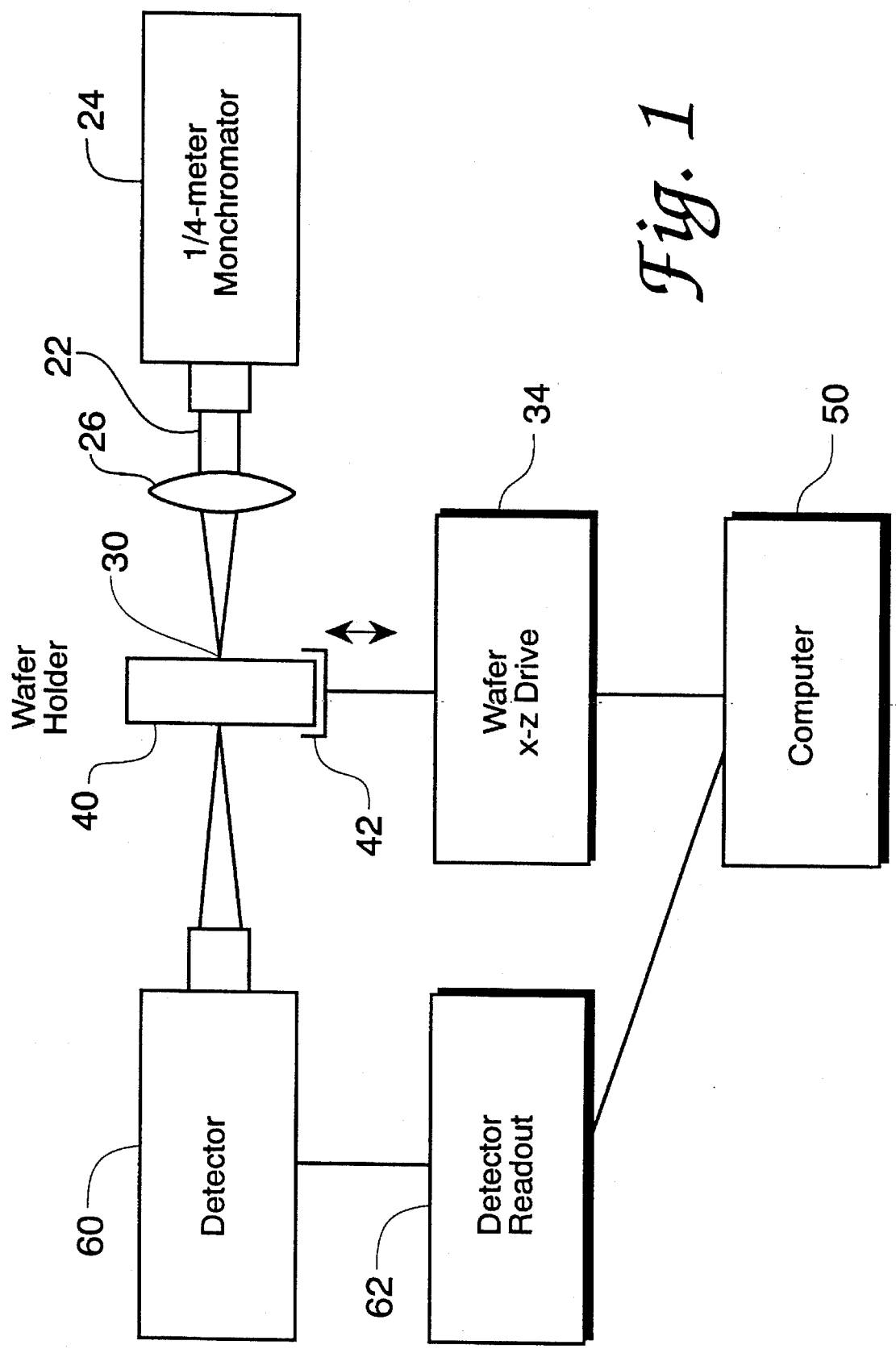
FIG. 1 is a block diagram of a system for automated measurement of the fractional transmission of light through a GaAs wafer.

The invention is an automated, digitized method for realizing nondestructively, whole-wafer dislocation maps of a polished conducting GaAs wafer. The measurement apparatus for achieving the maps may be substantially the same as the apparatus described in U.S. Pat. No. 5,008,542. A complete description of the apparatus is contained in U.S. Pat. No. 5,008,542 and therefore only the following brief description is provided here. With reference to FIG. 1, a beam of light 22 from a tungsten-halogen source (not shown) which has been apertured and focused through a ¼ meter Bausch and Lomb monochromator 24, is then refocused through a lens 26 into a square spot 30 on a sample wafer 40 positioned in a wafer holder 42. The size of the spot 30 is adjusted according to the desired spatial resolution. The wafer 40 is positioned by a motor driven actuator 34 under control of a computer 50. Resolution of the position encoders is 4 μm or better. Spot size is preferably 500 μm×500 μm for a total of up to 16,597 measurements on a three-inch wafer. Monochromatic light which passes through the sample wafer 40 is detected by a thermoelectricity cooled photovoltaic detector 60 operating in the low-noise zero-bias mode. The output is preferably lock-in detected for greater stability, and is coupled to a detector readout 62 which amplifies and digitizes the detected monochromatic light for input to computer 50. Dislocation maps may be generated by a plotter (not shown) connected to computer 50.

The method of the invention has been demonstrated with wafers grown by the vertical gradient freeze technique and doped with approximately $2 \times 10^{18}$ cm$^{-3}$ Si. The wafers are about 635 μm thick and polished on both sides. Transmission maps at wavelengths between 0.89 and 1.5 μm, with 0.02 μm resolution, were achieved by moving the wafers in controlled steps between the exit slit of the monochromator 24, and the detector 60. Signal to noise may be enhanced by chopping the light and using phase-sensitive detection.

Figure 2:
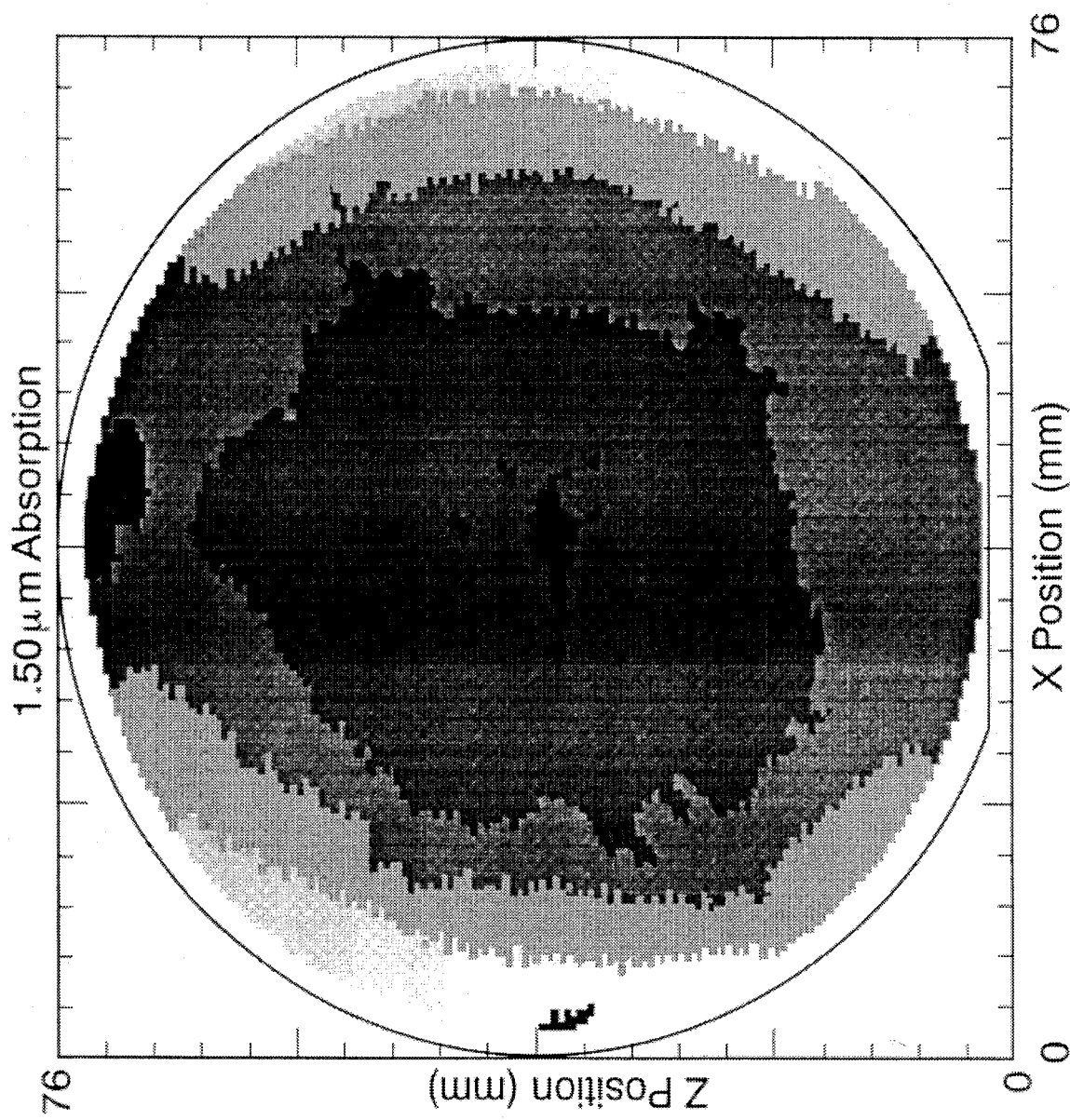
FIG. 2 is a gray-scale map showing absorption coefficient ($\alpha$) at $\lambda$= 1.5 µm in a GaAs:Si wafer with average carrier concentration $1.7 \times 10^{18}$ cm$^{-3}$.

To calibrate the values for dislocation density, a wafer was etched in molten KOH at 450° C., for 45 minutes producing a hexagonal pit at each point for which a dislocation intersects the surface. Both unetched and etched wafers were analyzed by the following formula:

$$T = \frac{(1-R)^2(1-S)^2 e^{-\alpha d}}{1 - R^2(1-S)^2 e^{-2\alpha d}} \quad (1)$$

where T is the relative transmission, S is the scattering factor (S≈0 for an unetched wafer), α is the absorption coefficient, d is the sample thickness, and R is the reflection coefficient. The reflection coefficient is given approximately by $R=(\eta-1)^2/(\eta+1)^2$ where η, the real part of the GaAs refractive index, can be determined from $$\eta = \left[ 7.10 + \frac{3.78}{1 - 0.18(h\nu)^2} \right]^{1/2} \quad (2)$$

at 300 K, where hν is the light energy in eV. It is well known that α∝n in GaAs for λ≧1 μm and n≧ $5 \times 10^{17}$ cm$^{-3}$. To check this relationship in GaAs:Si, transmission was measured and absorption calibrated from Eq. 1 at λ= 1.5 μm wavelength. The wavelength resolution was 0.0125 μm. Twenty-four 6-mm×6-mm square pieces were cut from representative areas of the wafer and a value for carder concentration (n) was determined for each piece by Hall-effect measurement. The values of n were compared with the respective average values of α (1.5 μm) calculated from Eq. 1 at the 144 positions (½-mm×½-mm resolution) corresponding to each 6-mm×6-mm square piece. The map of α at λ= 1.5 μm is shown in FIG. 2.

Figure 3:
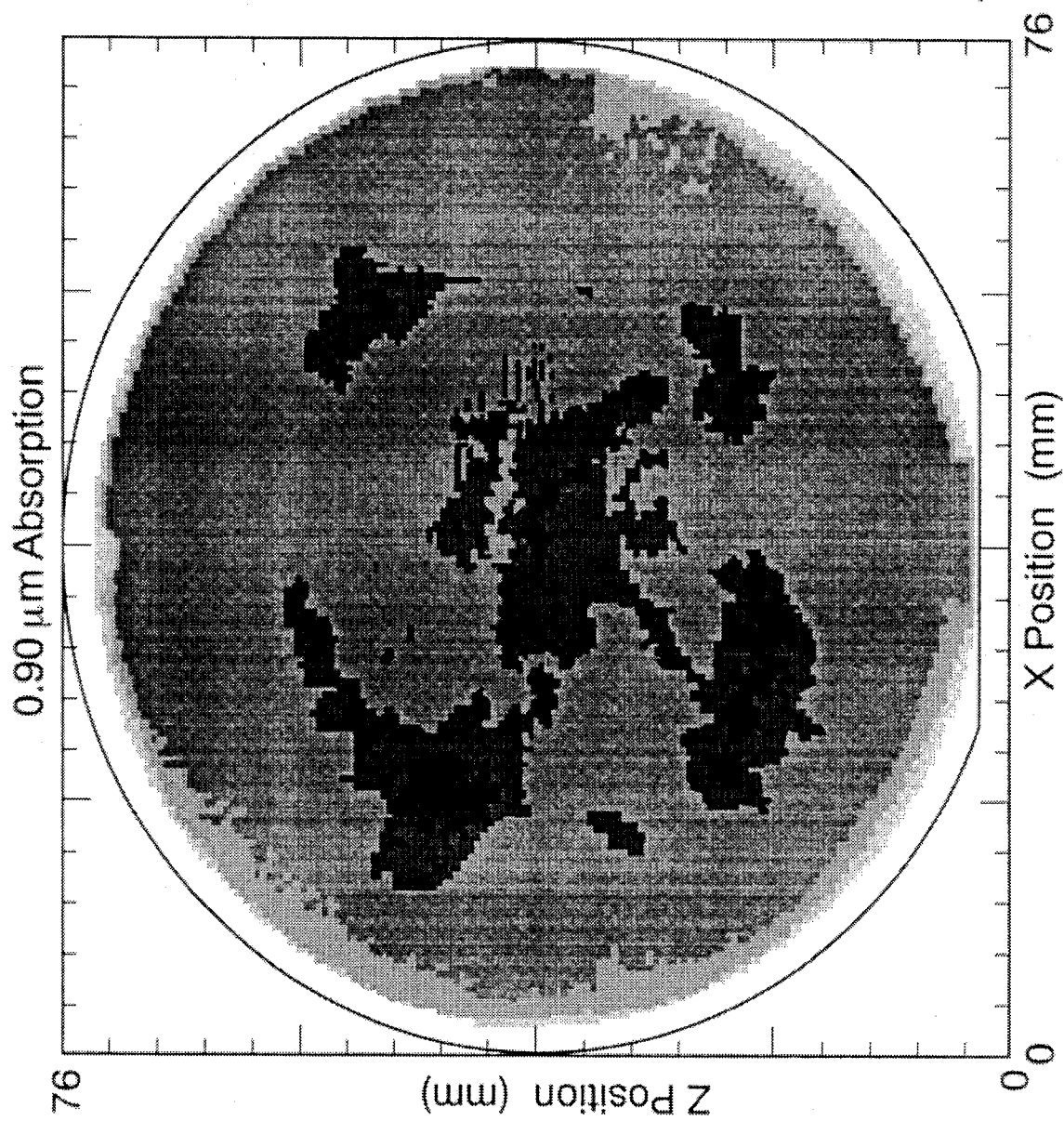
FIG. 3 is a gray-scale map showing absorption coefficient ($\alpha$) at $\lambda$= 0.90 µm in a GaAs:Si wafer with average carrier concentration $1.7 \times 10^{18}$ cm$^{-3}$.
Figure 4:
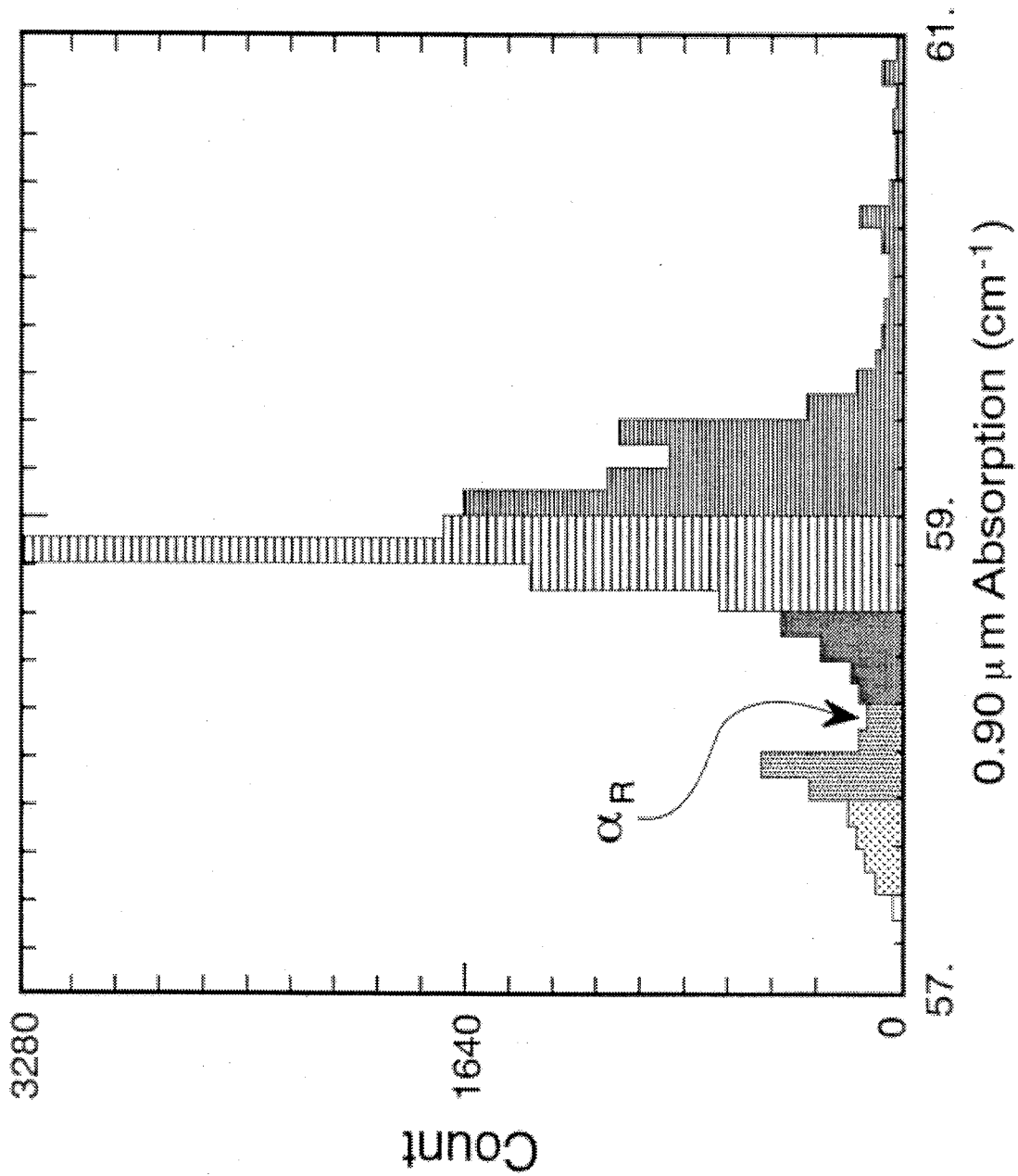
FIG. 4 is a histogram of the map of FIG. 3 at 0.90 µm absorption coefficient ($\alpha$)
Figure 5:
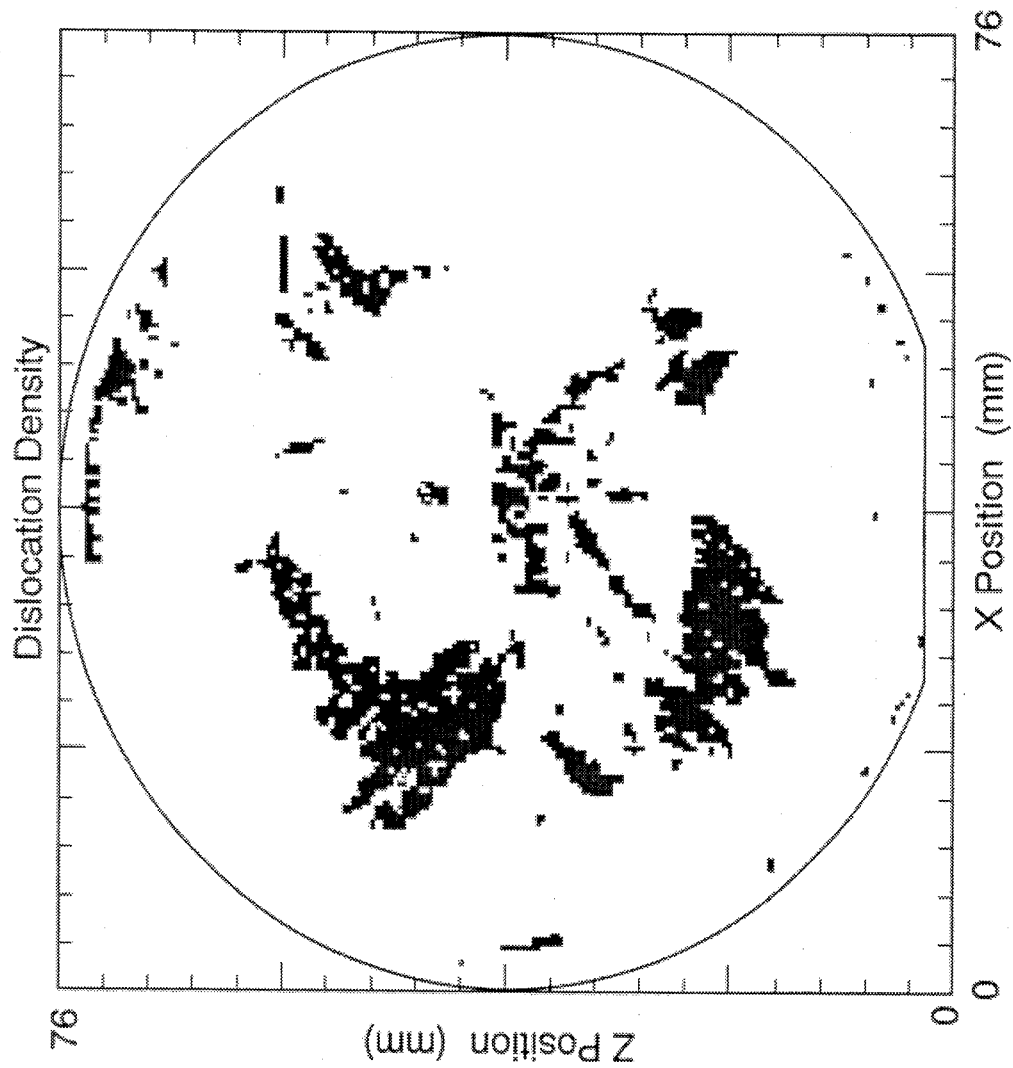
FIG. 5 is a black and white map of dislocation density showing regions of $\alpha$ at $\lambda$= 0.90 µm, with black comprising the region 57.3–58.1 cm$^{-1}$.

A similar map of absorption measured at a wavelength of 0.90 μm is shown in FIG. 3. A whole-wafer map of dislocation density may be nondestructively derived from absorption data measured at this wavelength by dividing the plurality of α values into equal segments between the maximum and minimum values of α, and plotting a histogram of the number of α values in each segment versus the value of α at the midpoint of the segment. A histogram of values for α at 0.90 μm is shown in FIG. 4. A value of α is selected which separates the lowest bell-shaped distribution in the histogram from the upper bell-shaped distribution. This reference α, referred to as $\alpha_R$, is generally the point in the histogram at which the first minimum occurs following the first maximum. The gray-scale map of α at 0.90 μm in FIG. 3 covers a range of 57 to 61 cm$^{-1}$. From the histogram of FIG. 4, the value of $\alpha_R$ was visually selected at 58.1 cm$^{-1}$. Positions on the wafer corresponding to points in which α is less than or equal to the reference $\alpha_R$ will indicate areas containing dislocations. A dislocation density map may be generated from the data by simply associating a color, for example black, to the coordinate (x,z) positions of all α's that are less than the reference $\alpha_R$, and a second color, for example white, to all α's that are greater than the reference $\alpha_R$. FIG. 5 shows a black and white map of whole-wafer dislocation density as inferred from the absorption date of FIG. 4. The map of FIG. 5 is intended only to be illustrative of the invention and other color schemes and arrangements may be contemplated within the scope of this invention.

Figure 6:
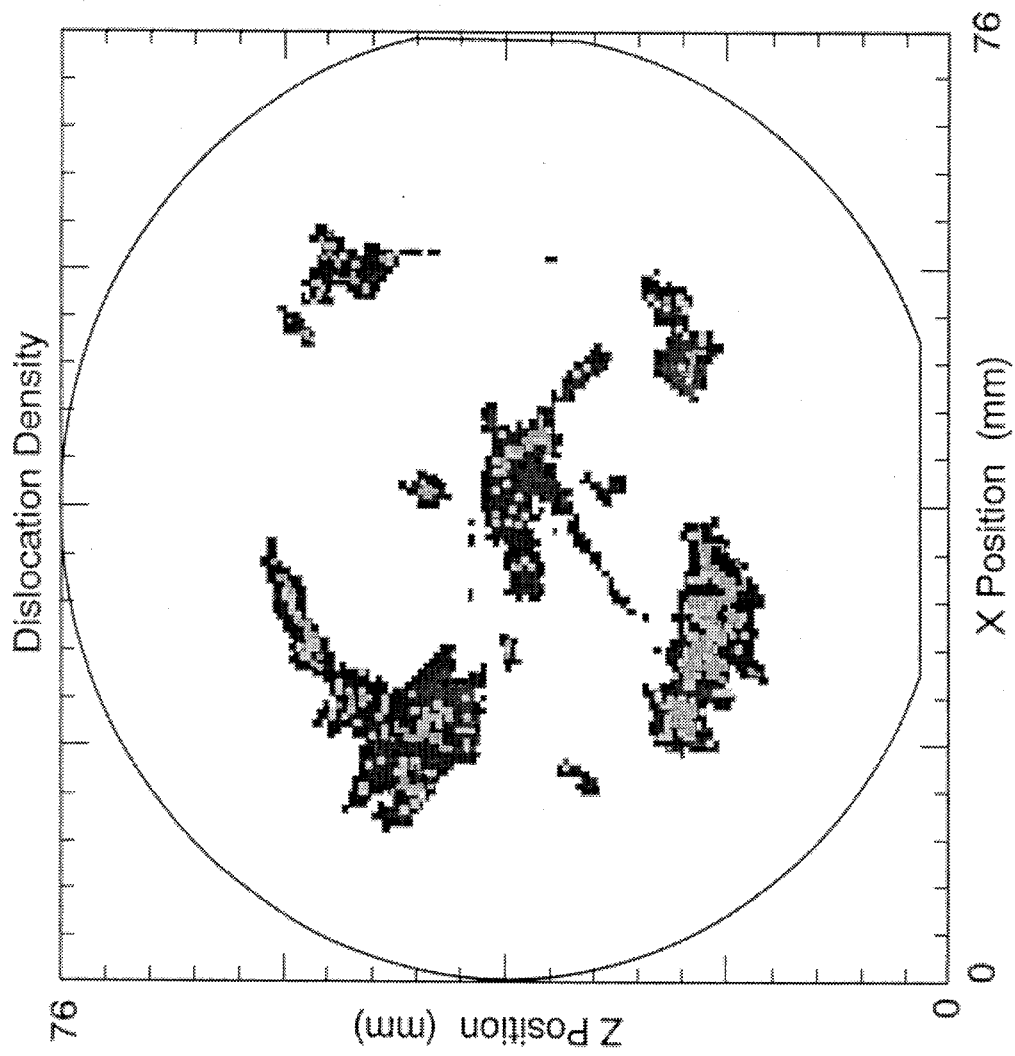
FIG. 6 is a gray-scale map of dislocation density showing visually counted etch pit density in an adjacent GaAs: Si wafer etched in molten KOH.

The above described method for nondestructively mapping whole-wafer dislocation density was confirmed by etching an adjacent wafer in KOH to delineate etch pits where dislocations intersect the surface, and analyzing the wafer again at 0.90 μm. Since this procedure affects only the surface, α remains the same, however, now S≠0, because the etch pits scatter the light. Since α is the same, Eq. 1 can be used to calculate the scattering factor S at each point. The etch pits were manually counted under a microscope and an etch pit density assigned to a number of locations. A calibration was effected by comparing the counted etch pit density with the scattering factor S at those locations. A resulting whole-wafer dislocation density map shown in FIG. 6 was determined at all locations by using this calibration to convert the measured 0.90 μm transmission of the etched wafer. The regions of low α in the unetched wafer absorption map of FIG. 3 correspond almost exactly with the regions of high scattering in the etched wafer map of FIG. 6. The same type of scattering calculation was also carried out for the 1.5 μm absorption data on the etched wafer. Observations under the microscope and manual etch pit density counting confirmed that the regions shown in FIG. 3 were the only regions with etch pits (maximum about 1500 cm$^{-2}$). The remaining areas of the wafer were generally dislocation free. Dislocated regions have a slightly higher n than the non-dislocated regions as may be directly observed from Hall-effect measurements, and indirectly seen from the absorption map at 1.5 μm (FIG. 2), for which α increases as n increases. The contrast is not high in the map of FIG. 2, as is apparent from the poor delineation of the dislocated region in the map itself, but in the maps of FIGS. 3, 5 and 6, the contrast is very high, clearly delineating the dislocated regions. The contrast has been found to be most pronounced at 0.90±0.03 μm, which is considered the optimal wavelength for nondestructively producing dislocation density maps according to the method of the invention.

Thus, while preferred features of the invention are described and illustrated herein, it is understood that changes and variations may be made by those skilled in the art without departing from the spirit and scope of the invention.

We claim:

1. A method for nondestructively producing a map of dislocation density in an unetched n+ type GaAs wafer, comprising the steps of:

a. focusing a light source of a predetermined wavelength at a plurality of points on said GaAs surface:

b. detecting the fractional transmission (T) of light through said GaAs surface at said plurality of points;

c. calculating from the detected value of T a value of the absorption coefficient ($\alpha$) at each of said plurality of points;

d. dividing the values of $\alpha$ into equal segments bounded by the minimum and the maximum values of $\alpha$;

e. plotting a histogram of the number of values of $\alpha$ in each segment versus the value of $\alpha$ at the midpoint of the segment;

f. selecting a reference point value from said histogram approximately at a point at which the first minimum value of $\alpha$ occurs following the first maximum value of $\alpha$; and g. generating a dislocation density map of said plurality of points such that the values of $\alpha$ that are less than the reference point value are in contrast with the values of $\alpha$ that are greater than the reference point value.

2. The method of claim 1, wherein said values of $\alpha$ that are less than the reference point value are indicated on said dislocation density map by a first color and the values of $\alpha$ that are greater than the reference point value are indicated by a second color.

3. The method of claim 1, wherein said light source has a wavelength of 0.90±0.03 µm.

* * * * *